United States Patent [19]

Nakagawa et al.

[11] Patent Number: 5,436,354
[45] Date of Patent: * Jul. 25, 1995

[54] INTERMEDIATES FOR PRODUCING ENYNE DERIVATIVES

[75] Inventors: Susumu Nakagawa; Akira Asai; Satoru Kuroyanagi; Makoto Ishihara; Yoshiharu Tanaka, all of Okazaki, Japan

[73] Assignee: Banyu Pharmaceutical Co., Ltd., Tokyo, Japan

[*] Notice: The portion of the term of this patent subsequent to Oct. 25, 2011 has been disclaimed.

[21] Appl. No.: 357,257

[22] Filed: Dec. 13, 1994

Related U.S. Application Data

[60] Continuation of Ser. No. 258,772, Jun. 13, 1994, which is a division of Ser. No. 153,956, Nov. 18, 1993, Pat. No. 5,359,091, which is a division of Ser. No. 974,488, Nov. 12, 1992, Pat. No. 5,296,612, which is a division of Ser. No. 861,160, Mar. 27, 1992, Pat. No. 5,231,183, which is a continuation of Ser. No. 588,931, Sep. 27, 1990, abandoned.

[30] Foreign Application Priority Data

Oct. 2, 1989 [JP] Japan .................................. 1-257310

[51] Int. Cl.$^6$ .................. C07C 211/24; C07D 333/58
[52] U.S. Cl. ...................................... 549/49; 564/387
[58] Field of Search ......................... 549/49; 564/387

[56] References Cited

U.S. PATENT DOCUMENTS

| | | | |
|---|---|---|---|
| 5,231,183 | 7/1993 | Nakagawa et al. | 549/49 |
| 5,296,612 | 3/1994 | Nakagawa et al. | 549/49 |
| 5,359,091 | 10/1994 | Nakagawa et al. | 549/49 |

FOREIGN PATENT DOCUMENTS 2110689 6/1983 United Kingdom .

OTHER PUBLICATIONS

Rudisill et al, Tetrahedron Letters, vol. 29, No. 13(1988) pp. 1509–1512.

*Primary Examiner*—Richard L. Raymond
*Attorney, Agent, or Firm*—Oblon, Spivak, McClelland, Maier, & Neustadt

[57] ABSTRACT

(E)-N-(3-Chloro-2-propenyl)-N-methyl-1naphthylenemethanamine and (E)-3-chloro-N-(3-chloro-2-propenyl)-N-methylbenzo[b]thiophene-7-methanamine which are useful as intermediates in the production of enyne compounds which exhibit squalene epoxidase inhibiting activity and anti-Eumycetes activity.

2 Claims, No Drawings

INTERMEDIATES FOR PRODUCING ENYNE DERIVATIVES

This is a continuation of application Ser. No. 08/258,772 filed on Jun. 13, 1994, which is a divisional of Ser. No. 08/153,956 filed on Nov. 18, 1993 now U.S. Pat. No. 5,359,091, which is a divisional of Ser. No. 07/974,488 filed on Nov. 12, 1992 now U.S. Pat. No. 5,296,612, which is a divisional of Ser. No. 07/861,160 filed on Mar. 27, 1992 now U.S. Pat. No. 5,231,183, which is a continuation of Ser. No. 07/588,931 filed on Sep. 27, 1990 now abandoned.

The present invention relates to a novel orocess for producing enyne derivatives. More particularly, it relates to a process for producing enyne derivatives which are useful for she preparation of compounds showing strong inhibiting activities against squalene.epoxidase of Eumycetes and thus being useful as anti-Eumycetes agents (typical example being Terbinafine: J. Med. Chem, 27, 1539 (1984)), compounds selectively inhibiting squalene.epoxidase of mammals and having strong anticholesterol activities (substituted alkyl amine derivatives; Japanese Patent Application No. 296840/1988) and their precursors.

Heretofore, the following methods have been known for the preparation of acetylene-conjugated allylamine derivatives. j. Med. Chem., 27, 1539 (1984) and Tetrahedron, 41, 5685 (1985) disclose a method for producing an acetylene-conjugated (E)-allylamine derivative by reducing with Dibai (diisobutylaluminum hydride) a conjugated 1,3-diynyl amine obtainable by coupling a terminal acetylene of a propargyl amine derivative with a bromoacetylene in the presence of copper chloride, or by subjecting a 1,3-diyne, a secondary amine and para-formaldehyde to Mannich reaction.

Tetrahedron Lett., 3145(1979) also discloses a method for obtaining an enyne derivative by a similar method. However, in these methods, at the same time as the formation of the desired product, a diene derivative is produced as a by-product in substantially the same amount as the desired product. Therefore, silica gel chromatography is required for the separation, and the yield of the (E)-enyne derivatives is low.

J. Med. Chem., 27, 1539 (1984) and the sections for starting materials in Japanese Unexamined Patent Publications No. 123177/1982, No. 146580/1983, No. 208252/1983, No. 23841/1988 and No. 313753/1988 disclose processes wherein an acetylene compound is lithiated with n-butyl lithium and then reacted by 1,2-addition with acrolein to obtain a secondary alcohol, and then an aqueous hydrogen bromide solution is reacted thereto to obtain a bromo derivative of an enyne, and then it is reacted with an amine. However, in these methods, the product is a mixture of E:Z=3:1. In order to isolate a desired (E)-enyne amine, silica gel chromatography is required.

In Tetrahedron Lett. 27, 1509 (1989), a secondary amine is lithiated at −78° C., then propargyi bromide is reacted thereto to obtain a propargyl amine derivative, which is then subjected to hydrozirconation with zirconocene chloride hydride, and then iodinated to an (E)-3-iodoallyl amine derivative. tert-Butylacetylene is lithiated and then reacted with tributylstannyl chloride at −78° C. to obtain tert-butylethynyttributylstannane, which is then subjected to cross coupling with the above-mentioned (E)-3-iodoallyl amine derivative to obtain an (E)-enyne amine derivative in good yield.

However, this method requires n-butyt lithium and a low temperature of −78° C. for the preparation of the propargyl amine derivative, and it also has a drawback that it requires a stoichiometric amount of such a special reagent as zirconocene chloride hydride.

It is an object of the present invention to develop an industrially advantageous process for producing an enyne derivative showing strong inhibiting activities against squalene.epoxidase of Eumycetes, an enyne derivative which selectively inhibits squaiene.epoxidase of mammals and which shows strong anti-cholesterol activities and intermediates for their preparation.

The present inventors have conducted an extensive research to accomplish such an object and as a result, have found a process for producing an acetylene-conjugated allytamine derivative in good yield at a low cost under a mild reaction condition while maintaining a stereo chemical structure of a double bond without requiring any special installation by reacting a substituted allylamine derivative of the formula (IV) with a substituted acetylene derivative of the formula (V) as described hereinafter in the presence of a palladium catalyst, preferabiv in the presence of a palladium catalyst, a copper salt and an organic amine or an inorganic base. The present invention has been accomplished on the basis of this discovery.

Further, they have found a synthesis for the substituted allylamine derivative of the formula (IV) and a series of new syntheses for an enyne derivative of the formula (VII) using this substituted allylamine derivative, whereby the present invention has been accomplished.

Thus, the present invention provides:

1. A process for producing an enyne derivative of the formula:

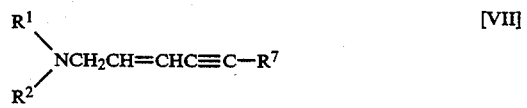

[VII]

wherein $R^1$ is a hydrogen atom, a lower alkyl group, a halo lower aikyl group, a lower alkenyl group, a lower alkynyl group or a cycloalkyl group, $R^2$ a hydrogen atom or a group of the formula:

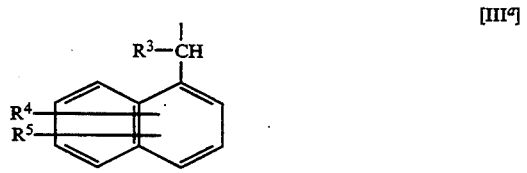

[III$^a$]

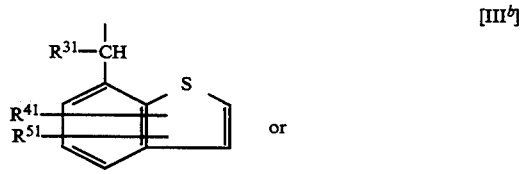

[III$^b$]

or

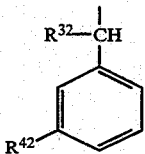
[III$^c$]

wherein each of $R^3$, $R^{31}$ and $R^{32}$ which may be the same or different, is a hydrogen atom or a lower alkyl group, each of $R^4$, $R^5$, $R^{41}$ and $R^{51}$ which may be the same or different, is a hydrogen atom, a halogen atom, a hydroxyl group, a lower alkyl group or a lower alkoxy group, $R^{42}$ is a hydroxyl group, a halogen atom, a group of the formula B—O— (wherein B is a protecting group for a hydroxyl group), a hydroxymethyl group, a formyl group, a carboxyl group, a lower alkoxycarbonyl group, a lower alkanoyl group, an amino group, a mercapto group or a group of the formula $R^6$—X—Y— (wherein $R^6$ is a phenyl or thienyl group which may have one or two substituents selected from the group consisting of a halogen atom, a hydroxyl group, a lower alkyl group, a cyano group, a lower alkoxy group and a heterocyclic group, each of X and Y which may be the same or different, is an oxygen atom, a sulfur atom, a carbonyl group, a group of the formula —CHR$^a$— (wherein R$^a$ is a hydrogen atom or a lower alkyl group) or a group of the formula —NR$^b$— (wherein R$^b$ is a hydrogen atom or a lower alkyl group), or X and Y together form a vinylene group or an ethynylene group), provided that when either one of X and Y is an oxygen atom, a sulfur atom or a group of the formula —NR$^b$— (wherein R$^b$ is as defined above), the other is a carbonyl group or a group of the formula —CHR$^a$— (wherein R$^a$ is as defined above), and $R^7$ is a lower alkyl or cycloalkyl group which may have a hydroxyl group or a lower alkoxy group, a phenyl group or a tri-tower alkylsilyl group, which process comprises reacting a compound of the formula:

[I]

wherein W is a halogen atom, and Z is a leaving group, with an amine of the formula:

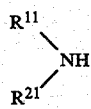
[II]

wherein $R^{11}$ is a hydrogen atom, a lower alkyl group, a halo lower alkyl group, a lower alkenyl group, a lower alkynyl group or a cycloalkyl group, and $R^{21}$ is a hydrogen atom or a group of the formula:

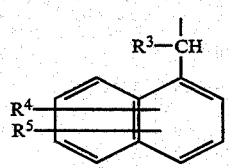
[III$^a$]

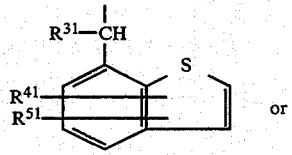
[III$^b$]

or

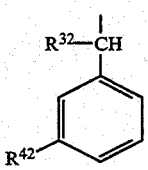
[III$^c$]

wherein $R^3$, $R^4$, $R^5$, $R^{31}$, $R^{32}$, $R^{41}$, $R^{42}$ and $R^{51}$ are as defined above, if necessary in the presence of a base, to obtain a compound of the formula:

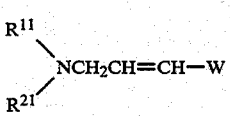
[IV]

wherein $R^{11}$, $R^{21}$ and W are as defined above, then reacting to this compound an acetylene derivative of the formula:

[V]

wherein $R^7$ is as defined above, in the presence of a palladium canalyst, to obtain a compound of the formula:

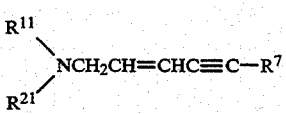
[VI]

wherein $R^{11}$, $R^{21}$ and $R^7$ are as defined above, and, if necessary, N-alkylating this compound.

2. The process for producing an enyne derivative of the formula:

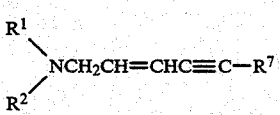
[VII]

wherein $R^1$, $R^2$ and $R^7$ are as defined above, which comprises reacting a compound of the formula:

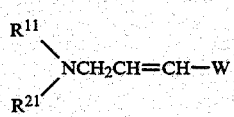
[IV]

wherein $R^{11}$, $R^{21}$ and W are as defined above with an acetylene derivative of the formula:

[V]

wherein $R^7$ is as defined above, in the presence of a palladium catalyst, to obtain a compound of the formula:

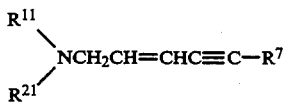

wherein $R^{11}$, $R^{21}$ and $R^7$ are as defined above, and, if necessary, N-alkylating this compound.

3. A compound of the formula:

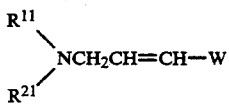

wherein $R^{11}$, $R^{21}$ and W are as defined above.

4. A process for producing a compound of the formula:

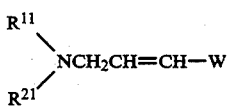

wherein $R^{11}$, $R^{21}$ and W are as defined above, which comprises reacting a compound of the formula:

$$Z-CH_2-CH=CH-W \qquad [I]$$

wherein W and Z are as defined above, with an amine of the formula:

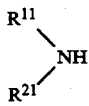

wherein $R^{11}$ and $R^{21}$ are as defined above.

The present invention has been accomplished based on the discovery of an industrially advantageous process for producing enyne derivatives which strongly inhibit squalene.epoxidase of Eumycetes or mammals and their intermediates.

Now, the definitions of terms used in this specification and their specific examples will be described.

The term "lower" is used to express that the number of carbon atoms of the group or compound modified with this term is at most 6, preferably at most 4.

Accordingly, the lower alkyl group may be a linear or branched alkyl group having from 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group or a hexyl group; the halo lower alkyl group may be a halo lower alkyl group having from 1 to 6 carbon atoms such as a fluoromethyl group, a trifluoromethyl group, a 2,2,2-trifluoroethyl group, a 2-chloroethyl group, a 3-fluoropropyl group, a 2-chlorobutyl group, a 5-fluoropentyl group or 6-chlorohexyl group; the lower alkenyl group may be a linear or branched alkenyl group having from 2 to 6 carbon atoms containing one or two double bonds in the carbon chain, such as a vinyl group, a 1-propenyl group, an isopropenyl group, an allyl group, a 1-methyl-1-propenyl group, a 2-methyl-1-propenyl group, a 1-methyl-2-propenyl group, a 2-methyl-2-propenyl group, a 1-butenyl group, a 2-butenyl group, a 3-butenyl group, a 1,3-butadienyl group, a 2-methyl-1-butenyl group, a 3-methyl-1,3-butadienyl group, a 2-ethyl-1-butenyl group, a 3-methyl-2-butenyl group, a 1-pentenyl group, a 2-pentenyl group, a 1,3-pentadienyl group, a 2,4-pentadienyl group, a 3-methyl-2-pentenyl group, a 1-hexenyl group or a 2-hexenyl group; and the lower alkynyl group may be a linear or branched alkynyl group having from 2 to 6 carbon atoms containing one or two triple bonds in the carbon chain, such as an ethynyl group, a 1-propynyl group, a propargyl group, a 1-butynyl group, a 2-butynyl group, a 3-butynyl group, a 3-methyl-1-butynyl group, a 3,3-dimethyl-1-butynyl group, a 1-pentynyl group, a 2-pentynyl group, a 3-pentynyl group, a 1,3-pentandiynyl group, a 1-ethynyl-2-propynyl group, a 4-methyl-2-pentynyl group or a 2-hexynyl group. The lower alkoxy group may be a linear or branched alkoxy group having from 1 to 4 carbon atoms such as a methoxy group, an ethoxy group, a propoxy group, an isopropoxy group, a butoxy group, an isobutoxy group, a sec-butoxy group or a tert-butoxy group, and the lower alkoxycarbonyl group may be a lower alkoxy carbonyl group having from 1 to 6 carbon atoms such as a methoxycarbonyl group, an ethoxycarbonyl group, a propoxycarbonyl group, a butoxycarbonyl group or a pentoxycarbonyl group. The lower alkanoyl group may be a lower alkanoyl group having from 2 to 6 carbon atoms such as an acetyl group, a propionyl group, a butyryl group, a pentanoyl group or a hexanoyl group. The tri-lower alkylsilyl group may be a tri-lower alkylsilyl group having from 3 to 8 carbon atoms such as a trimethylsilyl group or a tert-butyldimethylsilyl group. The halogen atom may be a fluorine atom, a chlorine atom, a bromine atom or an iodine atom. The leaving group for Z may be a halogen atom such as a chlorine atom, a bromine atom or an iodine atom, or an organic sulfonyloxy group such as a methanesulfonyloxy group or a p-toluenesulfonyloxy group. The cycloalkyl group may be a cycloalkyl group having from 3 to 7 carbon atoms such as a cyclopropyl group, a cyclobutyl group, a cyclopentyl group, a cyclohexyl group or a cycloheptyl group. The protecting group for a hydroxyl group represented by B may be the one which can readily be removed by hydrolysis under an acidic or alkaline condition, such as a methoxymethyl group, a tetrahydropyranyl group, a trityl group, a tert-butyldimethylsilyl group, a formyl group, an acetyl group, a methoxycarbonyl group, an ethoxycarbonyl group or a tert-butoxycarbonyl group.

The heterocyclic group may be a 5-12-membered, preferabely 5- or 6-membered heterocyclic group having from 1 to 3 hereto atoms selected from the group consisting of a nitrogen atom, an oxygen atom and a sulfur atom on its ring, such as a furyl group, a tetrahydrofuryl group, a pyrrolyl group, a pyrrolydinyl group, an imidazolyl group, a pyrazolyl group, an oxazolyl group, an isoxazolyl group, a furazanyl group, thiazolyl group, an isothiazolyl group, a thiadiazolyl group, a thienyl group, a pyridyl group, a piperidyl group, a pyrazinyl group, a pyrimidinyl group, a pyridazinyl group, a piperadinyl group, a morpholinyl group, a thiomorpholinyl group, a triazinyl group, a quinolyl group, an isoquinoiyl group, a phthalazinyl group, a naphthyridinyl group, a quinoxalinyl group, a quinazolinyl group, a benzofuranyl group, a benzothienyl group, a benzoisoxazolyl group, a benzothiazolyl group or a benzofurazanyl group.

X and Y may be the same or different as described above, and each represents an oxygen atom, a sulfur atom, a carbonyl group, a group of the formula —CHR$^a$— (wherein R$^a$ is a hydrogen atom or a lower alkyl group) or a group of the formula —NR$^b$— (wherein R$^b$ is a hydrogen atom or a lower alkyl group), or X and Y together represent a vinylene group or ethynylene group, provided that either one of X and Y is an oxygen atom, a sulfur atom or the group of the formula —NR$^b$—, the other represents a carbonyl group or the group of the formula —CHR$^a$—. Specifically, the group of the formula —X—Y— may be a group of the formula —(CHR$^a$)$_2$—, —CHR$^a$O—, —O-CHR$^a$—, CHR$^a$S—, —SHR$^a$—, CHR$^a$NR$^b$—, —NR$^b$CHR$^a$—, CHR$^a$CO—, —COCHR$^a$—, —COO—, —OCO—, —COS—, —SCO—, —CONR$^b$—, —NR$^b$CO—, —CH=CH—, —C≡C— (wherein R$^a$ and R$^b$ are as defined above).

The palladium catalyst is a catalyst useful for a palladium catalyst-cross coupling reaction (Accounts of Chemical Research, 12, 146–151 (1979); ditto, 15, 340–348 (1982); Angew. Chem. In,. Ed. Engl., 25, 508–524 (1986)) It may be a palladium-tertiary phosphine complex, as defined hereinafter, or a combination of a palladium salt and a tertiary phosphine or a combination of a palladium complex and a tertiary phosphine. The palladium-tertiary phosphine complex means a complex of zerovalent or bivalent palladium with a tertiary phosphine such as a trialkyl phosphine or a triaryl phosphine, and it may, for example, be tetrakis(-triphenylphosphine)palladium, bis(triphenylphosphine)palladium bromide, bis(triphenytphosphine)palladium chloride, acetoxybis(triphenylphosphine)palladium, benzylchlorobis(triphenylphosphine)palladium, tetrakis(tributylphosphine)palladium, bis(trimethylphosphine)palladium chloride, bis(triethylphosphine)palladium chloride, bis(tripropylphosphine)palladium chloride or bis(tributyiphospnine)palladium chloride. Preferred are tetrakis(triphenylphosphine)palladium, bis(triphenyiphosphine)palladium bromide, bis(triphenyiphosphine)paliadium chloride and acetoxybis(triphenylphosphine)palladium.

The palladium salt is a salt formed by a bivalent palladium ion and an acid residue, such as palladium chloride, palladium bromide, palladium acetate, palladium nitrate or palladium sulfate. Preferred are palladium chloride, palladium bromide and palladium acetate.

The palladium complex means, in addition to the above palladium-tertiary phosphine complex, other complexes of zerovalent or bivalent palladium. As such a complex, bis(phenylethylamine)palladium chloride, bis(benzonitrile)palladium chloride, bis(benzonitrile)palladium bromide or bis(acetonitrile)palladium chloride may be mentioned. Preferred are bis(benzonitrile)palladium chloride and bis(acetonitrile)palladium chloride.

The tertiary phosphine may be triphenyl phosphine, tributyl phosphine, tripropyl phosphine, triethyl phosphine or trimethyl phosphine. Preferred is triphenyl phosphine.

The copper salt means a monovalent or bivalent copper salt such as copper(I) chloride, copper(I) bromide, copper(I) iodide, copper(II) chloride, copper(II) bromide, or copper(II) iodide.

The organic amine may be a primary, secondary or tertiary alkylamine, or an aromatic amine, such as trimethylamine, triethylamine, diisopropylethylamine, diethylamine, diisopropylamine, ethylamine, isopropylamine amine, n-butylamine, isobutylamine, pyridine, N,N-dimethylaniline or 4-dimethylaminopyridine. The inorganic salt may be potassium hydroxide, sodium hydroxide, potassium hydrogen carbonate, sodium hydrogen carbonate, potassium carbonate or sodium carbonate.

When both or one of R$^{11}$ and R$^{21}$ of the formula [VI] is a hydrogen atom, the N-alkylation means, in addition to a reaction for introducing a lower alkyl group on N, a reaction for introducing a halo lower alkyl group, a lower alkenyl group, a lower alkynyl group or a cycloalkyl group on N as well as a reaction for introducing on N a group of the formula:

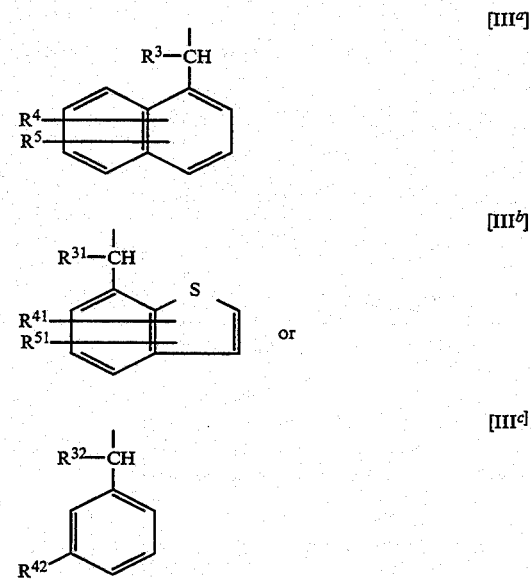

wherein R$^3$, R$^4$, R$^5$, R$^{31}$, R$^{32}$, R$^{41}$, R$^{42}$ and R$^{51}$ are as defined above.

Now, the process of the oresent invention will be described.

The process of the preset: invention comprises steps of the following reactions, or at least two continuous steps among them.

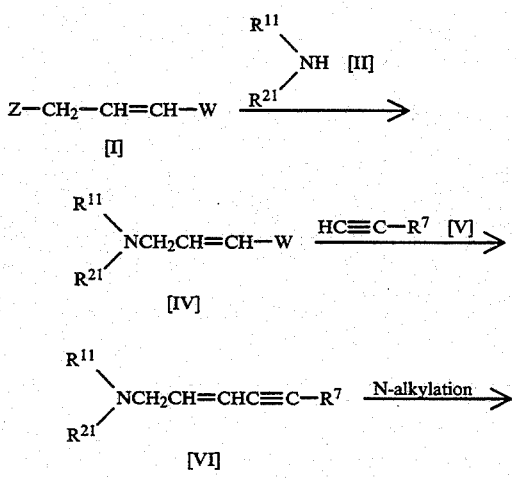

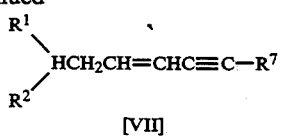

[VII]

The reaction of the compound of the formula [I] with the amine of the formula [II] is usually conducted by means of a suitable solvent, or the amine of the formula [II] may be used also as a solvent. The solvent to be used here is selected from solvents which do not adversely effect the reaction. As such a solvent, an alcohol such as methanol, ethanol, propanol or isopropyl alcohol, a halogenated hydrocarbon such as dichloromethane, chloroform or trichloroethane, an aromatic hydrocarbon such as benzene or toluene, a ketone such as acetone or methyl isobutyl ketone, tetrahydrofuran, dioxane, acetonitrile, dimethylformamide, dimethyl sulfoxide, or a mixture thereof or a mixture thereof with water, may be mentioned.

The reaction temperature is usually within a range of from $-10°$ C. to the boiling point of the solvent or to the boiling point of the amine, and the reaction time is usually from 30 minutes to 24 hours. However, such conditions are not necessarily limited to these ranges.

If necessary, a base may be employed. As such a base, an organic amine such as trimethyl amine, triethyl amine, pyridine, N,N-dimethylaniline or 4-dimethylaminopyridine, or an inorganic base such as potassium hydroxide, sodium hydroxide, potassium hydrogen carbonate, sodium hydrogen carbonate, potassium carbonate or sodium carbonate, may be mentioned.

The coupling reaction of the allylamine derivative of the formula [IV] having a halogen atom on a double bond with the substituted acetylene derivative of the formula [IV] is conducted in the presence of the above mentioned palladium catalyst, preferably in the presence of the palladium catalyst, a copper salt and an organic amine or an inorganic salt, if necessary by means of a suitable solvent.

The organic solvent useful for the reaction may be an alcohol such as methanol or ethanol, a halogenated hydrocarbon such as chloroform or dichloromethane, an aromatic hydrocarbon such as benzene or toluene, an ether such as diethyl ether, tetrahydrofuran or dioxane, or an aprotic polar solvent such as dimethylformamide, dimethyl sulfoxide or acetonitrile.

There is no particular restriction as to the amounts of the respective reagents used for the coupling reaction. Preferably, however, from 1 to 2 equivalent of the acetylene derivative of the formula [V] and from 0.005 to 0.1 equivalent of the palladium catalyst are used per equivalent of the allylamine derivative of the formula [IV]. Further, when the palladium catalyst is other than the palladium-tertiary phosphine complex, it is preferred to use from 0.01 to 0.2 equivalent of a tertiary phosphine per equivalent of the compound of the formula [IV], in addition to a palladium salt or a palladium complex.

The copper salt is preferably used in an amount of from 0.005 to 0.1 equivalent per equivalent of the compound of the formula [IV].

The organic amine may be used in large excess as a solvent. When an organic amine or an inorganic base is used in an organic solvent, such an organic amine or an inorganic base is used usually in an amount of from 1 to 5 equivalent per equivalent of the compound of the formula [IV].

Usually, the cross coupling reaction of the compound of the formula [IV] with the compound of the formula [V] is conducted in such a manner that the compound of the formula [IV], the palladium catalyst and the copper salt are added to the organic solvent, then to this mixture, the organic amine and the compound of the formula [V] are added preferably under stirring, followed by stirring usually at a temperature of from 0° to 150° C., preferably from 10° to 60° C. for from 0.5 to 24 hours.

The step for producing the compound of the formula [VII] by the N-alkylation of the compound of the formula [VI] corresponds to a step of the N-alkylation as defined above in a case where both or one of $R^{11}$ and $R^{21}$ in the formula [VI] is a hydrogen atom. When $R^{1l}$ and $R^{21}$ are both hydrogen atoms, the N-alkylation step may be repeated twice. This reaction is conducted by condensing the compound of the formula [VI] with an alkylating agent usually in a suitable solvent. The solvent to be used for this purpose is selected from solvents which do not adversely effect the reaction. A solvent may be an alcohol such as methanol, ethanol, propanol or isopropyl alcohol, a halogenated hydrocarbon such as dichloromethane, chloroform or trichoroethane, an aromatic hydrocarbon such as benzene or toluene, a ketone such as acetone or methyl isobutyl ketone, tetrahydrofuran, dioxane, acetonitrile, dimethylformamide, dimethyl sulfoxide, or a mixture thereof or a mixture thereof with water.

The reaction temperature is usually within a range of from $-10°$ C. to the boiling point of the solvent, and the reaction time is usually from 30 minutes to 24 hours. However, such conditions are not necessarily limited to these ranges.

Further, if necessary, a base may be employed. As such a base, an organic amine such as trimethylamine, triethylamine, pyridine, N,N-dimethylaniline or 4-dimethylamino pyridine, or an inorganic base such as potassium hydroxide, sodium hydroxide, potassium hydrogen carbonate, sodium hydrogen carbonate, potassium carbonate or sodium carbonate, may be mentioned.

The isolation and purification of the desired product in each of the above steps may be conducted by conventional isolation and purification methods such as extraction, recrystallization or chromatography. Depending upon the desired products, they may be isolated in the form of acid-addition salts such as hydrochlorides, sulfates or nitrates.

Now, the present invention will be described in further detail with reference to Examples and reference Examples. However, it should be understood that the present invention is by no means restricted to such specific Examples.

EXAMPLE 1

(E)-N-(6,6-Dimethyl-2-hepten-4-ynyl)propylamine hydrochloride

To a solution of 100 ml (1.21 mol) of n-propylamine in 170 ml of tetrahydrofuran was added 18.2 ml (0.198 mol) of 1,3-dichloropropene (E/Z=9/1) under ice cooling. The solution was stirred for 2 hours, and 1.90 g (0.01 mol) of copper (I) iodide, 709 mg (4.0 mmol) of palladium chloride, 2.10 g (8.0 mmol) of triphenylphosphine and 29.3 ml (0.238 mol) of tert-butylacetylene were added to the solution under ice cooling. The mixture was stirred for 20 hours at room temperature, and extracted with a mixture of 100 ml of ethyl acetate and 100 ml of water. The organic layer was washed with 100 ml of water. The aqueous layers were combined and extracted with 20 ml of ethyl acetate. A mixture of 200 ml of water and 6N hydrochloric acid was then added to the combined organic layers to adjust to pH 2. The aqueous layer was separated. The organic layer was extracted with 50 ml and 20 ml of water. The aqueous layers were combined, and washed with a mixture of 50 ml of ethyl acetate and 20 ml of n-hexane. The aqueous layer was treated with 200 ml of dichloromethane and then adjusted to pH 9 with 6N sodium hydroxide aqueous solution. The organic layer was separated and the aqueous layer was extracted with 20 ml of dichloromethane. The combined organic layers were washed with 50 ml of a saturated aqueous solution of sodium chloride and dried over anhydrous magnesium sulfate, and treated with 17% isopropylalcohol solution of hydrogen chloride. The solvent and excess hydrogen chloride were distilled off under reduced pressure to crystallize. The crystalline residue was suspended with a mixture of 30 ml of ethyl acetate and 50 ml of n-hexane. The crystals were collected by filtration and then dried under reduced pressure to obtain 25.0 g (yield: 59%) of the above identified compound as slightly yellowish brown crystalline powder.

Melting point: 190°–194° C. IR(KBr)cm$^{-1}$: 2970, 2930, 2770, 2720, 2500, 2410, 1630, 1455, 1360, 1260, 960 NMR(CDCl$_3$): 1.03(3H, t, 7Hz), 1.22(9H, s), 1.90(2H, q, 7Hz), 2,84(2H, bt), 3.63(2H, d, 7.5Hz), 5.89(1H, d, 15Hz), 6.22(1H, dt, 15Hz, 7.5Hz), 9.71(2H, bs).

EXAMPLE 2

(E)-N-(6,6-Dimethyl-2-hepten-4-ynyl)ethylamine hydrochloride

By using 145 ml (1.79 mol) of 70% ethylamine aqueous solution instead of n-propylamine, 255 ml of tetahydrofuran, 27.3 ml (0.296 mol) of 1,3-dichloropropene (E/Z =9/1), 2.85 g (15 mmol) of copper (I) iodide, 1.07 g (6.0 mmol) of palladium chloride, 3.15 g (12 mmol) of triphenylphosphine and 45.0 ml (0.365 mol) of tert-butylacetyiene, the treatment was conducted in the same manner as in Example 1 to obtain 44.4 g (yield: 74%) of the above identified compound as slightly yellowish brown crystalline powder.

Melting point: 172°–173° C. IR(KBr)cm$^{-1}$: 2970, 2930, 2700, 2470, 2370, 1630, 1455, 1360, 1260, 970,950, 800 NMR(CDCl$_3$)δ: 1.22(9H, s), 1.46(3H, t, 7Hz), 3.03(2H, q, 7Hz), 3.63(2H, d, 8Hz), 5.91(1H, d, 16Hz), 6.21(1H, dt, 16Hz, 8Hz), 9.74(2H, bs).

EXAMPLE 3

(E)-N-(6,6-Dimethyl-2-hepten-4-ynyl)methylamine hydrochloride

By using 104 ml (3.02 mol) of 40% methylamine aqueous solution instead of n-propylamine, 85 ml of tetrahydrofuran, 9.10 ml (98.8 mmol) of 1,3-dichloropropene (E/Z=9/1), 950 mg (5 mmol) of copper (I) iodide, 355 mg (2 mmol ) of palladium chloride, 1.05 g (4 mmol) of triphenylphosphine and 15.0 ml (0.121 mol) of tert-butylacetytene, the treatment was conducted in the same manner as in Example 1 to obtain 12.9 g (yield: 70%) of the above identified compound as off-white crystalline powder.

Melting point: 167° C. IR(KBr)cm$^{-1}$: 2970, 2770, 2720, 2440, 1470, 1460, 1440, 1360, 1270, 1200, 850 NMR(CDCl$_3$)δ: 1.22(9H, s), 2.66(3H, s), 3.64(2H, d, 8Hz), 5.92 ( 1H, d, 16Hz ), 6.18 ( 1H, d t, 16Hz, 8Hz ), 9.69(2H, bs).

EXAMPLE 4

(E)-N-(6-Methoxy-6-methyl-2-hepten-4-ynyl)ethylamine hydrochloride

To a solution of 232.4 ml (4.1 moi) of 70% ethylamin aqueous solution in 386 ml of tetrahydrofuran was added 43.4 ml (0.47 mol) of 1,3-dichioropropene (E/Z =9/1) under ice cooling. The solution was stirred for 2 hours at the same temperature and for one hour at room temperature. Then, 4.65 g (24.4 mmol) of copper (I) iodide, 1.74 g (9.8 mmol) of palladium chloride, 4.83 g (18.4 mmol) of triphenylphosphine and 20.0 g (0.204 mol) of 3-methoxy-3-methyl-t-butyne were added therein under ice cooling and the mixture was stirred at 30°–40° C. for 10 hours. The solvent was distilled off under reduced pressure and the residue was extracted with 300 ml of ethyl acetate. The organic layer was washed with 100 ml of saturated sodium chloride aqueous solution and 100 ml of 10% sodium carbonate aqueous solution, and then dried over anhydrous magnesium sulfate. The organic layer was concentrated under reduced pressure and the residue was distilled under reduced pressure to obtain 47 g of slightly yellow oil at 95° C./4 mmHg. The oil was dissolved in 100 ml of dichloromethane and 94 ml of 23% hydrogen chloride methanol solution was added thereto to acidify, and then the solvent was distilled off under reduced pressure. Precipitated crystals were suspended in ether, collected by filtration, washed with ether and then dried under reduced pressure to obtain 24.4 g (yield: 55%) of the above identified compound as slight purple crystalline powder.

Melting point: 139°–141° C. IR(KBr)cm$^{-1}$: 2990, 2940, 1660, 1630, 1550, 1430, 1410, 1320, 1010, 830 NMR(CDCl$_3$)δ: 1.45(9H, s), 1.47(3H, t, 7.5Hz), 3.02(2H, q, 75.Hz), 3.33(3H, s), 3.63(2H, d, 75.Hz), 5.95(1H, d, 15Hz), 6.30(1H, dr, 15Hz, 7.5Hz), 9.81(2H, bs).

EXAMPLE 5

(E)-3-Chloro-N-(3-chloro-2-propenyl)-N-methylbenzo[b]thiophene-7-methanamine

To a solution of 2.62 g-(10 mmol) of 7-bromomethyl-3-chlorobezo[b]thiophene in 10 ml of dimethyl sulfoxide were added 1.7 g (12 mmol) of (E)-N-(3-chloro-2-propenyl)methylamine hydrochloride and 2.07 g (15 mmol) of ground potassium carbonate. The mixture was stirred for 16 hours at room temperature, and poured into 150 ml of dichloromethane. The organic layer was washed with 100 ml ×2 of water and 50 ml of saturated sodium chloride aqueous solution, dried over anhydrous magnesium sulfate and then concentrated under reduced pressure. The residue was subjected to silica gel column chromatography (n-heptane). The desired fractions were put together and concentrated under reduced pressure to obtain 2.12 g (yield: 74%) of the above identified compound as an oil.

IR(KBr)cm$^{-1}$: 3100, 3055, 2790, 1635, 1505, 1455, 1395, 1325, 1045, 930, 785, 725 NMR(CDCl$_3$)δ: 2.24(3H, s), 3.10(2H, d, 6Hz), 3.79(2H, s), 6.08(1H, dt, 14Hz, 6Hz), 6.18(1H, d, 14Hz), 7.32(1H, s), 7.34(1H, d, 8Hz), 7.43(1H, t, 8Hz), 7.79(1H, d, 8Hz).

EXAMPLE 6

(E)-3-Chloro-N-(3-chloro-2-propenyl)-N-methylbenzo[b]thiophene-7-methanamine To a solution of 0.22 g (1.0 mmol) of 3-chloro-N-methylbenzo[b]thiophene-7-methanamine in 3 ml of dimethyl sulfoxide were added 0.12 ml (1.2 mmol) of 1,3-dichloropropene (E/Z=9/1) and 0.21 g (1.5 mmol) of ground potassium carbonate. The mixture was stirred for 17 hours at 50° C., and poured into 50 ml of ethyl acetate. The organic layer was washed with 25 ml ×2 of water and 10 ml of saturated sodium chloride aqueous solution, dried over anhydrous magnesium sulfate and then concentrated under reduced pressure. The residue was subjected to silica gel chromatography (n-heptane→n-heptane/ethyl acetate=9/1). The desired fractions were put together and concentrated under reduced pressure to obtain 0.21 g (yield: 73%) of the above identified compound as an oil.

IR and NMR data of the isolated compound agreed with those of Example 5 compound.

EXAMPLE 7

(E)-N-(3-Chloro-2-propenyl)-N-ethyl-3-hydroxybenzylamine

To a solution of 34.96 g (0.231 mol) of N-ethyl-3-hydroxybenzylamine in 200 ml of dimethylsulfoxide were added 25.64 g (0.231 mol) of 1,3-dichloropropene (E/Z=2/1) and 16.7 g (0.121 mol) of ground potassium carbonate under ice cooling. The mixture was stirred for 4 hours at 50° C., poured into 250 ml of ethyl acetate, washed with 200 ml ×2 of water and 200 ml of saturated sodium chloride aqueous solution, dried over anhydrous magnesium sulfate and then concentrated under reduced pressure. The residue was subjected to-silica gel chromatography (n-hexane→n-hexane/ethyl acetate =9/1). The desired fractions were put together and concentrated under reduced pressure to obtain 26.2 g (yield: 50%) of the above identified compound as an oil.

IR(KBr)cm$^{-1}$: 2970, 2820, 1600, 1590, 1460, 1270, 780, 690 NMR(CDCl$_3$)δ: 1.06(3H, t, 7Hz), 2.56(2H, q, 7Hz), 3.12(2H, d, 6.5Hz), 3.54(2H, s), 4.9(1H, bs), 6.00(1H, dr, 13Hz, 6.5Hz), 6.14(1H, d, 13Hz), 6.7–6.9(3H, m), 7.18(1H, t, 8Hz).

EXAMPLE 8

(E)-N-(3-Chloro-2-propenyl)-N-propyl-3-hydroxybenzylamine

To a solution of 3.30 g (20 mmol) of N-propyl-3hydroxybenzylamine in 20 ml of dimethyl sulfoxide were added 1.82 g (20 mmol) of 1,3-dichloropropene (E/Z =2/1) and 1.38 g (10 mmol) of ground potassium carbonate under ice cooling. The mixture was stirred for 1.5 hours at room temperature and for 3 hours at 50° C., poured into 70 ml of ethyl acetate, washed with 50 ml ×2 of water and 50 ml of saturated sodium chloride aqueous solution, dried over anhydrous magnesium sulfate and then concentrated under reduced pressure. The residue was subjected to silica gel chromatography (n-hexane→n-hexane/ethyl acetate =9/1). The desired fractions were put together and concentrated under reduced pressure to obtain 2.29 g (yield: 48%) of the above identified compound as an oil.

IR(KBr)cm$^{-1}$: 2950, 2800, 1590, 1460, 1270, 930, 790, 690 NMR(CDCl$_3$)δ: 0.85(3H, t, 7Hz), 1.51(2H, q, 7Hz), 2.43(2H, t, 7Hz), 3.09(2H, d, 7Hz), 3.53(2H, s), 6.2(1H, bs), 6.00 (1H, dt, 14Hz, 7Hz), 6.12(1H, d, 14Hz), 6.7–6.9(3H, m), 7.18(1H, t, 8Hz).

EXAMPLE 9

(E)-N-(3-Chloro-2-propenyl)-N-ethyl-3-bromobenzylamine

To a solution of 4.28 g (20 mmol) of N-ethyl-3-bromobenzylamine in 30 ml of N,N-dimethylformamide were added 2.44 g (22 mmol) of 1,3-dichloropropene and 1.70 g (12 mmol) of ground potassium carbonate under ice cooling. The mixture was stirred for 8 hours at 60° C., poured into 40 ml of ethyl acetate, washed with 40 ml ×2 of water and 40 ml of saturated sodium chloride aqueous solution, dried over anhydrous magnesium sulfate and then concentrated under reduced pressure. The residue was subjected to silica gel chromatography (n-hexane→n-hexane/ethyl acetate =9/1). The desired fractions were put together and concentrated under reduced pressure to obtain 3.70 g (yield: 64%) of the above identified compound as an oil.

IR(KBr)cm$^{-1}$: 2970, 2800, 1570, 1430, 1360, 1070, 930, 780, 670 NMR(CDCl$_3$)δ: 1.04(3H, t, 7Hz), 2.52(2H, q, 7Hz), 3.09(2H, d, 7Hz), 3.54(2H, s), 5.98(1H, dt, 14Hz, 7Hz), 6.13(1H, d, 14Hz), 7.1–7.6(3H, m).

EXAMPLE 10

(E)-N-(3-Chloro-2-propenyl)-N-methyl-1-naphthalenemethanamine

To a solution of 9.84 g (57.5 mmol) of N-methyl-1-naphthalenemethanamine in 60 ml of dimethyl sulfoxide were added 5.5 ml (60 mmol) of 1,3-dichloropropene (E/Z =9/1) and 8.28 g (60 mmol) of potassium carbonate under ice cooling. The mixture was stirred for 6 hours at room temperature, poured into 250 ml of ethyl acetate, washed with 150 ml ×3 of water and 150 ml of saturated sodium chloride aqueous solution, dried over anhydrous magnesium sulfate and then concentrated under reduced pressure. The residue was subjected to silica gel chromatography (n-hexane→n-hexane/ethyl acetate =9/1). The desired fractions were put together and concentrated under reduced pressure to obtain 10.86 g (yield: 77%) of the above identified compound as an oil.

IR(KBr)cm$^{-1}$: 3050, 2950, 2840, 2790, 1630, 1510, 1460, 1365, 1130, 1020, 930, 790, 770
NMR(CDCl$_3$)δ2.23(3H, s), 3.10(2H, d, 6.5Hz), 3.89(2H, s), 6.06(1H, dt, 13Hz, 6.5Hz), 6.17(1H, d, 13Hz), 7.4–8.3(7H, m).

EXAMPLE 11

(E)-N-(3-Chloro-2-propenyl)propylamine hydrochloride

To 19.7 ml (0.24 mol) of n-propylamine was added 1.82 ml (20 mmol) of 1,3-dichloropropene (E/Z =9/1) under ice cooling. The mixture was stirred for 3 hours at the same temperature, and concentrated under reduced pressure to remove n-propylamine. The residue was treated with 50 ml of ethyl acetate and precipitated n-propylamine hydrochloride was filtered and washed with 10 ml of ethyl acetate. The filtrate and washing were combined, washed with 20 ml of saturated sodium hydrogen carbonate aqueous solution and 20 ml of water and 20 ml of saturated sodium chloride aqeous solution, dried over anhydrous magnesium sulfate, and then concentrated under reduced pressure. The yellow residual oil was dissolved in 4 ml of 23% hydrogen chloride methanol solution. The solvent and excess hydrogen chloride were distilled off under reduce pressure. The resulting crystals were suspended in 8 ml of diisopropyl ether, filtered, washed with 1 ml ×2 of diisopropyl ether and then dried to obtain 2.38 g (yield 70%) of the above identified compound as slightly yellowish brown crystalline powder.

Melting point: 216°–218° C. IR(KBr)cm$^{-1}$: 2970, 2800, 2730, 2680, 2520, 2430, 1640, 1460, 1020, 940, 880, 810, 780, 750 NMR(CDCl$_3$)δ: 0.93(3H, t, 7Hz), 1.63(2H, q, 7Hz), 2.80(2H, t, 7Hz), 3 59(2H, d, 7Hz), 6.14(1H, dr, 14Hz, 7Hz), 6.78(1H, d, 14Hz), 9.3(2H, bs).

EXAMPLE 12

(E)-N-13-Chloro-2-propenyl)ethylamine hydrochloride

To 38.6 ml (0.48 mol) of ethylamine was added 3.64 ml (40 mmol) of 1,3-dichloropropene (E/Z =9/1) under ice cooling. The mixture was stirred for 4 hours at the same temperature. Thereto, 30 ml of dichloromethane was added and the mixture was washed with 20 ml of water, dried over anhydrous magnesium sutfate, and then concentrated under atmospheric pressure. The residue was dissolved with 15 ml of 20% hydrogen chloride methanol solution, and concentrated under reduced pressure to remove the solvent and excess hydrogen chloride. The resulting crystals were suspended in 6 ml of ethyl acetate, filtered and dried to obtain 4.85 g (yield: 78%) of the above identified compound as slightly yellowish brown crystalline powder.

Melting point: 148°–149° C. IR(KBr)cm$^{-1}$: 2960, 2800, 2750, 2450, 1640, 1590, 1455, 1040, 940, 800 NMR(CDCl$_3$)δ: 1.47(3H, t, 7Hz), 3.06(2H, q, 7Hz), 3.65(2H, d, 7Hz), 6.17(1H, dr, 14Hz, 7Hz), 6.59(1H, d, 14Hz), 9.76(2H, bs).

EXAMPLE 13

(E)-N-(6,6-Dimethyl-2-hepten-4-ynyl)-N-methyl-1-naphthalenemethanamine hydrochloride (terbinafine)

To 33 ml of tetrahydrofuran were added 5.40 g (22 mmol) of (E)-N-(3-chloro-2-propenyl)-N-methyl-1-naphthalenemethanamine, 210 mg (1.1 mmol) of copper (I) iodide and 356 mg (0.31 mmoi) of tetrakis (triphenylphospnine)palladium, and further, 4.35 ml (44 mmol) of n-butylamine and 2.83 mt (23.1 mmol) of tert-butylacetylene under ice cooling. The mixture was stirred for 17 hours at room.temperature. The reaction mixture was concentrated and the residue was subjected silica gel chromatography (n-hexane→n-hexane/ethyl acetate =9/1→4/1). The desired fractions were put together and concentrated under reduced pressure. The oily residue was dissolved in 6 ml of ethanol and 6 ml 23% hydrogen chloride methanol solution was added thereto. The solvent and excess hydrogen chloride were distilled off. The resulting crystals were suspended in diisopropyl ether, filtered, washed with diisopropyl ether and dried to obtain 6.41 g (yield: 89%) of the above identified compound as white crystalline powder.

Melting point: 205° C. IR(KBr)cm$^{-1}$: 2970, 2440, 1465, 1410, 1360, 955, 805, 770 NMR(CDCl$_3$+D$_2$O)δ: 1.23(9H, s), 2.60(3H, s), 3.72(2H, d, 7.5Hz), 4.62(2H, s), 5.87(1H, d, 15Hz), 6.37(1H, dt, 15Hz, 7.5Hz), 7.5–8.2(7H, m).

EXAMPLE 14

(E)-N-(6,6-Dimethyl-2-hepten-4-ynyl)-N-ethyl-3-hydroxybenzylamine

To 30 ml of tetrahydrofuran were added 4.51 g (20 mmol) of (E)-N-(3-chloro-2-propenyl)-N-ethyl-3-hydroxybenzylamine, 190.5 mg (1 mmol) of copper (I) iodide and 324 mg (0.28 mmoi) of tetrakis (triphenyiphospnine)palladium, and further, 3.95 ml (40 mmol) of n-butyiamine and 2.94 ml (24 mmol) of tert-butylacetylene under ice cooling. The mixture was stirred for 20 hours at room temperature. The reaction mixture was concentrated under reduced pressure and the residue was subjected to silica gel chromatography (n-hexane→n-hexane/ethyl acetate =7/3). The desired fractions were put together and concentrated under reduced pressure to oil. The oil was cooled to crystallize and the crystals were suspended in cooled n-hexane. The crystals were collected by filtration and then dried to obtain 4.20 g (yield: 77%) of the above identified compound as slightly yellow crystalline powder.

Melting point: 72°–74° C. IR(KBr)cm$^{-1}$: 2970, 1600; 1460, 1360, 1260, 1240, 960, 860, 800, 760 NMR(CDCl$_3$)δ: 1.05(3H, t, 7Hz), 1.24(9H, s), 2.53(2H, q, 7Hz), 3.12(2H, d, 6.5Hz), 3.53(2H, s), 4.4(1H, bs), 5.66(1H, d, 16Hz), 6.10(1H, dt, 16Hz, 6.5Hz), 6.7–6.9(3H, m), 7.17(1H, t, 8Hz).

EXAMPLE 15

(E)-N-(6,6-Dimethyl-2-hepten-4-ynyl)-N-ethyl-3-hydroxybenzylamine

By using 89.8 mg (0.4 mmol) of palladium acetate and 210 mg (0.8 mmol) of triphenyiphosphine instead of tetrakis(triphenylphosphine)palladium, the treatment was conducted in the same manner as in Example 14 to obtain 4.63 g (yield: 85%) of the above identified compound as slightly yellow crystalline powder.

Melting point, IR and NMR data of the isolated compound agreed with those of Example 14 compound.

EXAMPLE 16

(E)-N-(6,6-Dimethyl-2-hepten-4-ynyl)-N-ethyl-3-hydroxybenzylamine

By using 70.9 mg (0.4 mmol) of palladium chloride and 210 mg (0.8 mmol) of triphenylphosphine instead of tetrakis(triphenylphosphine)palladium, the treatment was conducted in the same manner as in Example 14 to obtain 4.51 g (yield: 83%) of the above identified compound as slightly yellow crystalline powder.

Melting point, IR and NMR data of the isolated compound agreed with those of Example 14 compound.

EXAMPLE 17

(E)-N-(6,6-Dimethyl-2-hepten-4-ynyl)-N-ethyl-3-bromobenzylamine

To 10 ml tetrahydrofuran were added 1.44 g (5 mmol) of (E)-N-(3-chloro-2-propenyl)-N-ethyl-3-bromobenzylamine, 47.6 mg (0.25 mmol) of copper (I) iodide and 22.4 mg (0.1 mmol) of palladium acetate and 52.5 mg (0.2 mmol) of triphenylphosphine, and further, 1.0 ml (10 mmol) of n-butylamine and 0.74 ml (6 mmol) of tert-butylacetylene under ice cooling. The mixture was stirred for 20 hours at room temperature, and concentrated under reduced oressure. The residue was subjected to silica gel chromatography (n-hexane→n-hexane/ethyl acetate =20/1). The desired fractions were put together and concentrated under reduced pressure to obtain 1.37 g (yield: 82%) of the above identified compound as an oil.

IR(KBr)cm$^{-1}$: 2970, 2800, 1595, 1570, 1470, 1450, 1260, 1260, 960, 770, 670 NMR(CDCl$_3$)δ: 1.05(3H, t, 7Hz), 1.26(9H, s), 2.53(2H, q, 7Hz), 3.12(2H, d, 6.5Hz), 3.54(2H, s), 5.68(1H, d, 16Hz), 6.12(1H, dt, 16Hz, 6.5Hz ), 7.1–7.6(4H, m).

EXAMPLE 18

(E)-N-(6,6-Dimethyl-2-hepten-4-vnyl)-N-propyl-3-hydroxybenzylamine

To 12.5 ml of tetrahydrofuran were added 2.00 g (8.34 mmol) of (E)-N-(3-chloro-2-propenyl)-N-propyl-3-hydroxybenzylamine, 79.4 mg (0.417 mmol) of copper (I) iodide, 37.4 mg (0.167 mmol) of palladium acetate and 87.5 mg (0.334 mmol) of triphenylphosphine, and further, 1.65 mi (16.7 mmol) of n-butylamine and 1.23 ml (10.0 mmol) of tert-butylacetylene under ice cooling. The mixture was stirred for 20 hours at room temperature, and concentrated under reduced pressure. The residue was subjected to silica gel chromatography (n-hexane→n-hexane/ethyl acetate =19/1→9/1). The desired fractions were put together and concentrated under reduced pressure to oil. The oil was cooled to crystallize and the crystals were suspended in cooled n-hexane. The crystals were collected by filtration and then dried to obtain 2.13 g (yield: 89%) of the above identified compound as slightly yellow crystalline powder.

Melting point: 79°–80° C. IR(KBr)cm$^{-1}$: 2990, 2810, 1580, 1480, 1335, 1285, 1265, 1240, 980, 850, 780, 750, 700, NMR(CDCl$_3$ )δ: 0.85(3H, t, 7Hz), 1.24(9H, s), 1.50(2H, q, 7Hz), 2.41(2H, t, 7Hz), 3.12(2H, d, 6.5Hz), 3.53(2H, s), 5.1(1H, bs), 5.66(1H, d, 16Hz), 6.11(1H, dt, 16Hz, 6.5Hz), 6.7–6.9(3H, m), 7.17(1H, t, 7.5Hz).

EXAMPLE 19

(E)-N-(6-Hydroxy-6-methyl-2-hepten-4-ynyl)-N-ethyl-3-hydroxybenzylamine

To 7.5 ml tetrahydrofuran were added 1.13 g (5 mmol) of (E)-N-(3-chloro-2-pentenyl)-N-ethyl-3hydroxybenzylamine, 4.76 mg (0.25 mmol) of copper (I) iodide, 18.0 mg (0.1 mmol) of palladium chloride and 52.5 mg (0.2 mmol) of triphenyiphosphine, and further, 0.99 ml (10 mmol) of n-butylamine and 0.58 ml (6 mmol) of 3-methyl-1-butyne-3-ol under ice cooling. The mixture stirred for 20 hours at room temperature. The reaction mixture was concentrated under reduced pressure and the residue was subjected to silica gel chromatography (n-hexane→n-hexane/ethyl acetate =3/2 ). The desired fractions were put together and concentrated under reduced pressure to obtain 1.07 g (yield: 78%) of the above identified compound as an oil.

IR(KBr)cm$^{-1}$: 3400, 2980, 2930, 2800, 1600, 1590, 1450, 1360, 1240, 1160, 950, 690 NMR(CDCl$_3$)δ: 0.98(3H, t, 7Hz), 1.37(9H, s), 2.40(2H, q, 7Hz), 3.08(2H, d, 6.5Hz), 3.40(2H, s), 5.18(1H, s), 5.63(1H, d, 15.5Hz), 5.98(1H, dt, 15.5Hz, 6.5Hz), 6.4–6.7(3H, m), 6.98(1H, t, 7Hz ), 9.07(1H, s).

EXAMPLE 20

(E)-N-(6-Methyl-2-octen-4-ynyl)-N-ethyl-3-[3-(3-thieny)benzyloxy]benzylamine

To a solution of 100 mg (0.25 mmol) of (E)-N-(3-chloro-2-propenyl)-N-ethyl-3-[3-(3thienyl)benzyl)benzyloxy]benzylamine in 2 ml of tetrahydrofuran were added 6.0 mg (0.023 mmol) of triphenylphosphine, 4.0 mg (0.023 mmol) of palladium chloride, 6.0 mg (0.032 mmol) of copper (I) iodide, 100 μl (1 mmol) of n-butylamine and 0.5 ml (5.12 mmol) of 3-methyl-1-pentyne. The mixture was stirred for 48 hours at room temperature and concentrated under reduced oressure. The residue was treated with a mixture of ethyl acetate and water. The organic layer was separated, washed with water, dried over anhydrous magnesium sulfate and concentrated under reduced pressure. The residue was subjected to silica gel chromatography (n-hexane→n-hexane/ethyl acetate =9/1). The desired fractions were put together and concentrated under reduced pressure. The residue was subjected to thin layer chromatography to obtain 79 mg (yield: 71%) of the above identified compound as a brown oil.

IR( KBr)cm$^{-1}$: 2970, 2930, 2870, 2800, 1600, 1490, 1460, 1380, 1340, 1260, 1150, 1090, 1040, 960, 850, 770, 690 NMR(CDCl$_3$)δ: 0.98(3H, t, 7Hz), 1.03(3H, t, 7Hz), 1.16(3H, d, 7Hz), 1.47(2H, qui., 7Hz), 2.49(3H, m), 3.08(2H, d, 7.5Hz), 3.54(2H, s), 5.10(2H, s), 5.64(1H, d, 16Hz), 6.18(1H, dt, 16Hz, 7.5Hz), 6.8–7.7(11H, m).

EXAMPLE 21

(E)-N-(2-Octen-4-ynyl)-N-ethyl-3-[3-(3-thienyl)benzyloxy]benzylamine

To a solution of 100 mg (0.25 mmol) of (E)-N-(3-chloro-2-propenyl )-N-ethyl-3-[3-( 3-thienyl)benzyloxy]benzylamine in 2 ml of tetrahydrofuran were added 5.6.mg (0.021 mmol) of triphenylphosphine, 5.0 mg (0.028 mmol) of palladium chloride, 6.0 mg (0.032 mmol) of copper (I) iodide, 100 μl (1.0 mmol) of n-butylamine and 464 μl (4.8 mmol) of 1-pentyne. The mixture was stirred for 24 hours at 40° C. The same work-up and purification as in Example 20 gave 59 mg (yield: 55%) of the above identified compound as a brown oil.

IR(KBr)cm$^{-1}$: 3110, 3030, 2970, 2930, 2870, 2800, 1580, 1490, 1460, 1380, 1340, 1260, 1150, 1090, 1040, 960, 880, 850, 770, 690 NMR(CDCl$_3$ )δ: 0.99(3H, t, 7Hz), 1.03(3H, t, 7Hz), 1.55(2H, sex., 7Hz), 2.27(2H, t, 7Hz), 2.50(2H, q, 7Hz), 3.09(2H, d, 7.5Hz), 3.54(2H, s), 5.10(2H, s), 5.63(1H, d, 16Hz), 6.10(1H, dt, 16Hz, 7.5Hz), 6.8–7.7(11H, m).

EXAMPLE 22

(E)-N-(6,6-Dimethyl-2-hepten-4-ynyl)-N-ethyl-3-[4-(3-thienyl)-2-thienylmethyoxy]benzylamine To 10 ml of tetrahydrofuran were added 1.01 g (2.5 mmol) of (E)-N-(3-chloro-2-propenyl)-N-ethyi-3-[4-(3-thienyl)-2-thienylmethyoxy]benzylamine, 23.8 mg (0.125 mmol) of copper (I) iodide, 8.9 mg (0.05 mmol) of palladium chloride and 26.2 mg (0.1 mmol) of triphenylphosphine, and further 0.50 ml (5.0 mmol) of n-butylamine and 0.37 ml (3.0 mmol) of tert-butylacetylene under ice cooling. The mixture was stirred for 17 hours at room temperature, and extracted with a mixture of 70 ml of ethyl acetate and 30 ml of water. The organic layer was separated, washed with a mixture of 40 ml of water and 4 ml of 2N hydrochloric acid, a mixture of 40 ml of water and 6 ml of saturated sodium bicarbonate aqueous solution and 20 ml of saturated sodium chloride aqueous solution and then dried over anhydrous magnesium suifate. After ethyl acetate was evaporated under reduced pressure, the residue was treated with 3 ml of methanol, and stirred for 17 hours under ice cooling.

The resulting crystals were collected by filtration, washed with 2 ml of methanol and dried under reduced pressure to obtain 0.81 g (yield: 72%) of the above identified compound as slightly yellowish brown crystalline powder.

Melting point: 52°–57° C. IR(KBr)cm$^{-1}$: 3100, 2960, 2920, 2800, 1610, 1580, 1480, 1440, 1360, 1260, 1040, 960, 790, 750 NMR(CDCl$_3$)δ: 1.02(3H, t, 7Hz), 1.23(9H, s), 2.52(2H, q, 7Hz), 3.10(2H, d, 7Hz ), 3.55(2H, s), 5.23(2H, s), 5.66(1H, d, 16Hz), 6.10(1H, dt, 16Hz, 7Hz), 6.82–7.10(3H, m), 7.18–7.50(6H, m).

EXAMPLE 23

(E)-3-Chloro-N-(6,6-dimethyl-2-hepten-4-ynyl)-N-methylbenzo[b]thiophene-7-methanamine hydrochloride To a solution of 0.86 g (3.0 mmol) of (E)-3-chloro-N-(3-chloro-2-propenyl)-N-methylbenzo[b]thiophene-7-methanamine in 5 ml of tetrahydrofuran were added 42.6 mg (0.16 mmol) of triphenylphosphine, 20.1 mg (0.11 mmol) of palladium chloride, 34.0 mg (0.18 mmol) of copper (I) iodide, 0.6 ml (6.1 mmol ) of n-butylamine and 0.5 ml (4.1 mmol) of tert-butylacetylene. The mixture was stirred for 24 hours at room temperature, poured into 40 ml of ethyl acetate. The organic layer was separated, washed with 20 ml ×2of water, dried over anhydrous magnesium sulfate and concentrated under reduced pressure. The residue was subjected to silica gel chromatography (n-heptane→n-heptane/ethyl acetate =5/1). The desired fractions were put together and concentrated under reduced pressure. The residue was treated with 3 ml of 23% hydrogen chloride methanol solution and the solution was concentrated. The resulting crystals were suspended in isopropylalcohol, filtered, washed with isopropylalcohol and dried to obtain 0.77 g (yield: 70%) of the above identified compound as white crystalline powder.

Melting point: 202° C. IR(KBr)cm$^{-1}$: 3100, 2960, 2555, 2500, 2225, 1630, 1505, 1460, 1400, 1325, 1040, 965, 785 725, NMR(CDCl$_3$ )δ: 1.23(9H, s), 2.69(3H, s), 3.63–3.66(2H, m), 4.26–4.58(2H, m), 5.88( 1H, d, 16Hz), 6.36( 1H, dt, 16Hz, 8Hz), 7.40(1H, s), 7.66(1H, t, 8Hz), 7.96(1H, d, 8Hz), 8.20(1H, d, 8Hz), 13.2(1H, bs).

EXAMPLE 24

(E)-N-(6,6-Dimethyl-2-hepten-4-ynyl)-propylamine hydrochloride

To 7.5 ml of tetrahydrofuran were added 850 mg (5 mmol) of (E)-N-(3-chloro-2-propenyl)propylamine hydrochloride, 47.6 mg (0.25 mmol) of copper (I) iodide, 22.4 mg (0.1 mmol) of palladium acetate and 52.5 mg (0.2 mmol) of triphenylphosphine, and further, 1.48 ml (15 mmol) of n-butylamine and 0.74 ml (6 mmol) of butylacetylene under ice cooling. The mixture was stirred for 20 hours at room temperature, and concentrated under reduced pressure. The residue was subjected to silica gel chromatography (n-hexane→n-hexane/ethyl acetate =3/2). The desired fractions were put together and concentrated under reduced pressure. The residue was dissolved with 15 ml of 23% hydrogen chloride methanol solution, and the solvent and excess hydrogen chloride were distilled off. The resulting crystals were suspended in 3 ml of a mixture of ethyl acetate and diisopropyl ether (1/1), filtered, washed with 1 ml of the same solvent and dried to obtain 780 mg (yield: 72%) of the above identified compound as slightly yellowish brown crystalline powder.

Melting point, IR and NMR data of the isolated compound agreed with those of Example 1 compound.

EXAMPLE 25

(E)-N-(6,6-Dimethyl-2-hepten-4-ynyl)ethylamine hydrochloride

To 15 ml of tetrahydrofuran were added 1.56 g (10 mmol) of (E)-N-(3-chloro-2-propenyl)ethylamine hydrochloride, 95.2 mg (0.5 mmol) of copper (I) iodide, 44.9 mg (0.2 mmol) of palladium acetate and 105 mg (0.4 mmol) of triphenylphosphine, and further, 2.97 ml (30 mmol) of n-butylamine and 1.47 ml (12 mmol) of tert-butylacetylene under ice cooling. The mixture was stirred for 18 hours at room temperature, and concentrated under reduced pressure. The residue was subjected to silica gel chromatography (n-hexane→n-hexane/ethyl acetate =9/1→3/7). The desired fractions were put together and concentrated under reduced pressure. The residue was dissolved in 3 ml of 17% hydrogen chloride isopropyl alcohol solution, and the solvent and excess hydrogen chloride were distilled off. The resulting crystals were suspended in 20 ml of a mixture of ethyl acetate and diisopropyl ether (1/3), cooled, filitered, washed with 5 ml of diisopropyl ether and dried to obtain 1.46 g (yield: 72%) of the above identified compound as off-white crystalline powder.

Melting point, IR and NMR data of the isolated compound agreed with those of Example 2 compound.

EXAMPLE 26

(E)-N-(6,6-Dimethyl-2-hepten-4-ynyl)-N-ethyl-3-[3-(3-thienyl)benzyloxy]benzylamine hydrochloride To 2.7 ml of tetrahydrofuran were added 360 mg (0.90 mmol) of (E)-N-(3-chloro-2-propenyl)-N-ethyl-3-[3-(3-thienyl)benzyloxy]benzylamine, 8.6 mg (0.045 mmol) of copper (I) iodide, 4.1 mg (0.018 mmol) of palladium acetate and 9.5 mg (0.036 mmol) of triphenylphosphine, and further, 0.18 ml (1.8 mmol) of n-butylamine and 0.135 ml (1.08 mmol) of tert-butylacetylene under ice cooling. The mixture was stirred for 24 hours at room temperature, and concentrated under reduced pressure. The residue was subjected to silica gel chromatography (n-hexane→n-hexane/ethyl acetate =9/1). The desired fractions were put together and concentrated under reduced pressure to obtain 340 mg (yield: 85%) of the above identified compound as an oily free amine.

NMR(CDCl$_3$)δ: 1.02(3H, t, 7Hz), 1.23(9H, s), 2.51(2H, q, 7Hz), 3.10(2H, d, 7.5Hz), 3.54(2H, s), 5.11(2H, s), 5.65(1H, d, 16Hz), 6.08(1H, dt, 16Hz, 7.5Hz), 6.9–7.8(11H, m).

The oily free amine was dissolved in 1 ml of 17% hydrogen chloride isopropyl alcohol solution, and the solvent and excess hydrogen chloride were distilled off. The residue was cooled to crystallize. The crystals were suspended in 10 ml of a mixture of chloroform and n-hexane (1/10), filtered, washed with 2 ml of n-hexane and dried under reduced pressure to obtain 300 mg (yield: 89%) of the above identified compound as white crystalline powder.

Melting point: 163°–165° C. IR(KBr)cm$^{-1}$:2970, 2500, 1600, 1460, 1440, 1265, 1170, 1025, 960, 775, 760, 745, 690 NMR(CDCl$_3$+D$_2$O)δ:23(9H, s), 1.39(3H, t, 7Hz ), 3.0(2H, bm), 3.6(2H, bm), 4.08(2H, s), 5.22(2H, s), 5.81(1H, d, 16Hz), 6.21(1H, dt, 16Hz, 8Hz), 7.0–7.8(11H, m).

EXAMPLE 27

(E)-N-(6,6-Dimethyl-2-hepten-4-ynyl)-N-methyl-1-naphthalenemethanamine hydrochloride (terbinafine)

To a solution of 1.77 g (10 mmol) of 1-chloromethyl-naphthalene in 10 ml of dimethyl sulfoxide were added 1.88 g (10 mmol) of (E)-N-(6,6-dimethyl-2-hepten-4-ynyl)methylamine hydrochloride and 1.66 g (12 mmol) of potassium carbonate under ice cooling. The mixture was stirred for 16 hours at room temperature, poured into 200 ml of ethyl acetate, washed with 100 ml ×2 of water, a mixture of 80 ml of water and 10 ml of 2N hydrochloric acid, and 50 ml of saturated sodium chloride aqueous solution respectively, dried over anhydrous magnesium sulfate and concentrated under reduced pressure to crystallize. The crystals were suspended in 10 ml of ethyl acetate, cooled, filtered and dried under reduced pressure to obtain 2.95 g (yield: 90%) of the above identified compound as off-white crystalline powder.

Melting point, IR and NMR data of the isolated compound agreed with those of Example 13 compound.

EXAMPLE 28

(E)-3-Chloro-N-(6,6-dimethyl-2-hepten-4-ynyl)-N-methylbenzo[b]thiophene-7-methanamine hydrochloride To a solution of 0.34 g (1.3 mmol) of 7-bromomethyl-3-chlorobenzo[b]thiophene in 3 ml of dimethyl sulfoxide were added 0.246 g (1.31 mmol) of (E)-N-(6,6-dimethyl-2-hepten-4-ynyl)methylamine hydrochloride, and 0.27 g (1.95 mmol) of potassium carbonate under ice cooling. The mixture was stirred for 19 hours at room temperature, poured into 40 ml of dichloromethane, washed with 30 ml ×2 of water, and adjusted to pH 2 with 25 ml of water and 2N hydrochloric acid. The organic layer was separated washed with 20 ml of saturated sodium chloride aqueous solution, dried over anhydrous magnesium sulfate, concentrated under reduced pressure and cooled to crystallize. The crystals were suspended in isopropylalcohol, filtered, washed with isopropyl alcohol and dried to obtain 0.37 g (yield: 77%) of the above identified compound as white crystalline powder.

Melting point, IR and NMR data of the isolated compound agreed with those of Example 23 compound.

REFERENCE EXAMPLE 1

(E)-N-(3-chloro-2-propenyl)-N-ethyl-3-[3-(3thienyl)-benzyloxy]benzylamine

To a solution of 280 mg (1.24 mmol) of (E)-N-(3-chloro-2-propenyl)-N-ethyl-3-hydroxybenzylamine in 2.5 ml of tetrahydrofuran was added 74.4 mg (1.86 mmol) of 60% oily sodium hydride under ice cooling. The mixture was stirred for 20 minutes at room temperature, ice-cooled, treated with a solution of 333 mg (1.24 mmol) of 3-(3-thienyl)benzyl mesylate in 2.5 ml of dimethylformamide, and stirred for 1.5 hours at room temperature. The reaction mixture was poured into 40 ml of ethyl acetate, washed with 20 ml ×2 of water and 20 ml of saturated sodium chloride aqueous solution, dried over anhydrous magnesium sulfate and concentrated under reduced pressure. The residue was subjected to silica gel chromatography (n-hexane→n-hexane/ethyl acetate =9/1). The desired fractions were put together and concentrated under reduced pressure to obtain 460 mg (yield: 93%) of the above identified compound as an oil.

IR(KBr)cm$^{-1}$: 2970, 2925, 1595, 1580, 1485, 1460, 1260, 1150, 1035, 770, 690 NMR(CDCl$_3$)δ: 1.04(3H, t, 7Hz), 2.52(2H, q, 7Hz), 3.09(2H, d, 7Hz), 3.56(2H, s), 5.12(2H, s), 5.98(1H, dt, 7Hz, 14Hz), 6.11(1H, d, 14Hz), 6.8–7.7(11H, m).

REFERENCE EXAMPLE 2

(E)-N-(3-chloro-2-propenyl)-N-ethyl-3-[4-(3-thienyl)-2-thienylmethoxy]benzylamine To a solution of 2.26 g (10 mmol) of (E)-N-(3-chloro-2-propenyl)-N-ethyl-3-hydroxybenzylamine in 14 ml of tetrahydrofuran was added 0.48 g (12 mmol) of 60% oily sodium hydride under ice cooling. The mixture was stirred for 10 minutes at room temperature, ice-cooled, treated with a solution of 2.59 g (10 mmol) of 2-bromomethyl-4-(3-thienyl)thiophene in 10 ml of dimethylformamide, and stirred for 2 hours at room temperature. The reaction mixture was poured into 150 ml of ethyl acetate, washed with 100 ml ×2 of water and 50 ml of saturated sodium chloride aqueous solution, dried over anhydrous magnesium sulfate and concentrated under reduced pressure. The residue was subjected to silica gel chromatography (n-heptane/dichloromethane). The desired fractions were put together and concentrated under reduced pressure to obtain 3.11 g (yield: 77%) of the above identified compound.

IR(KBr)cm$^{-1}$: 3100, 2960, 2920, 2800, 1600, 1580, 1480, 1440, 1370, 1260, 1150, 1030, 840, 780, 740 NMR(CDCl$_3$)δ: 1.04(3H, t, 7Hz), 2.53(2H, q, 7Hz), 3.09(2H, d, 7Hz), 3.54(2H, s), 5.22(2H, s), 6.00(1H, dt, 7Hz, 14Hz), 6.11(1H, d, 14Hz), 6.84–7.12(3H, m), 7.20–7.50(6H, m).

We claim:

1. A compound of the formula:

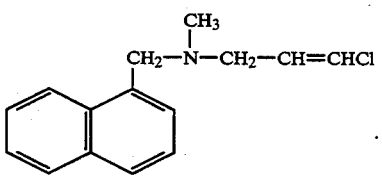

2. A compound of the formula:

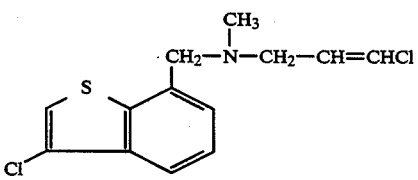

* * * * *